(12) United States Patent
Tanabe et al.

(10) Patent No.: US 8,895,246 B2
(45) Date of Patent: Nov. 25, 2014

(54) NUCLEIC ACID DETECTION METHOD

(75) Inventors: Maiko Tanabe, Tokyo (JP); Chihiro Uematsu, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 870 days.

(21) Appl. No.: 11/332,527

(22) Filed: Jan. 17, 2006

(65) Prior Publication Data

US 2006/0223085 A1  Oct. 5, 2006

(30) Foreign Application Priority Data

Mar. 30, 2005  (JP) ................. 2005-099179

(51) Int. Cl.
*C12P 19/34* (2006.01)
*C12Q 1/68* (2006.01)

(52) U.S. Cl.
CPC ............... *C12P 19/34* (2013.01); *C12Q 1/6865* (2013.01)
USPC ...... 435/6.12; 435/91.1; 435/91.2; 435/91.51

(58) Field of Classification Search
USPC .................. 435/6, 91.1, 91.2, 91.51, 6.12
See application file for complete search history.

(56) References Cited

U.S. PATENT DOCUMENTS

| | | | | |
|---|---|---|---|---|
| 5,130,238 A | * | 7/1992 | Malek et al. ................ | 435/91.21 |
| 2004/0171041 A1 | * | 9/2004 | Dahl et al. ................ | 435/6 |
| 2004/0197802 A1 | * | 10/2004 | Dahl et al. ................ | 435/6 |
| 2004/0209291 A1 | | 10/2004 | Uematsu et al. | |
| 2006/0188896 A1 | * | 8/2006 | Seul et al. ................ | 435/6 |

FOREIGN PATENT DOCUMENTS

| | | |
|---|---|---|
| JP | 11-000198 | 1/1999 |
| WO | WO 87/06270 | 10/1987 |
| WO | WO 91/01384 | 2/1991 |
| WO | WO 02/061140 A2 * | 8/2002 |

OTHER PUBLICATIONS

Leone et al., "Molecular beacon probes combined with amplification by NASBA enable homogenous, real-time detection of RNA," Nucleic Acids Research, 1998, vol. 26, No. 9, pp. 2150-2155.*
Walker et al., "Strand displacement amplification—an isothermal, in vitro DNA amplification technique," Nucleic Acids Research, 1992, vol. 20, No. 7, pp. 1691-1696.*
Wikipedia, "Transcription (genetics)," dowloaded from website, http://en.wikipedia.org/wiki/transcription_(genetics), Oct. 20, 2008, p. 1-6.*
Proc. Natl. Acad. Sci. USA vol. 86, pp. 9717-9721, Dec. 1989, Biochemistry.
Primer-Directed Enzymatic Amplification of DNA With a Thermostable DNA Polymerase; Randall K. Salki et al. 239, 487-491, 1988.
J. Compton, et al., nature, 350, 91-92, 1991.
G.T. Walker, et al., Proc. Natl. Acad, Sci USA, 89, 392-396, 1992.
J.C. Guatelli, et al. Proc Natl. Acad. Sci. USA, 87, 1874-1878, 1990.
Notice of Rejection for corresponding Japanese application No. 2005-099179; Issue date: Mar. 9, 2010.
Self-sustained Sequence Replication (3SR): An Isothermal Transcription-based Amplification System Alternative to PCR; E. Fahy, D.Y. Kwoh, and T.R. Gingeras; PCR Methods and Applications, vol. 1, pp. 25-33 (1991).

* cited by examiner

*Primary Examiner* — Kenneth R. Horlick
*Assistant Examiner* — Joyce Tung
(74) *Attorney, Agent, or Firm* — Antonelli, Terry, Stout & Kraus, LLP.

(57) ABSTRACT

This invention provides a novel method for amplifying and detecting a target gene rapidly with high sensitivity under isothermal conditions. In such method, a sequence to be amplified can be freely designed regardless of the template sequence, an amplified product can be amplified and detected within a short period of time with high sensitivity, and thus, the gene expression level can be determined more easily than is possible with prior art.

6 Claims, 10 Drawing Sheets

NUCLEIC ACID DETECTION METHOD

CLAIM OF PRIORITY

The present application claims priority from Japanese application JP 2005-099179 filed on Mar. 30, 2005, the content of which is hereby incorporated by reference into this application.

TECHNICAL FIELD

The present invention relates to a nucleic acid (DNA or RNA) detection method that is useful in genetic analysis. More particularly, the present invention relates to a method for detecting specific genes of viruses, prokaryotes, eukaryotes, and the like.

BACKGROUND ART

In the field of biological sciences, amplification of DNA or RNA has been carried out for various purposes. For example, competitive PCR (A. Wang, et al., Proc. Natl. Acad. Sci. USA, 86, 9717-9721, 1989) and real-time PCR (S. H. Aliyu, et al., Journal of Antimicrobial, 54, 968, 2004) have been known as techniques for analyzing the expression of given genes and quantifying the expression levels thereof. These techniques involve the application of a common nucleic acid amplification technique, i.e., polymerase chain reaction (PCR) (R. K. Saiki, et al., Science, 239, 487-491, 1988), to determine expression levels based on the amplified genes.

The aforementioned nucleic acid amplification technique for analysis consists of 3 steps of denaturation from double-strand template DNA to single-strand template DNA, annealing of the primers to the single-strand template DNA, and elongation of complimentary strands from the primers. It can also consist of 2 steps of denaturation and elongation. Such amplification technique requires repetition of a cycle from high temperature treatment to low temperature treatment.

In order to carry out such a cycle, it is necessary to carry out PCR with the use of a thermal cycler that is capable of accurate temperature control. An increased number of cycles results in a prolonged time frame required for bringing the temperature of the apparatus and that of the reaction solution to the determined levels. This disadvantageously prolongs the time frame required for analysis.

In order to overcome such drawbacks, nucleic acid amplification techniques that could be carried out under isothermal conditions were developed. Examples of major techniques that have been known include nucleic acid sequence-based amplification (NASBA) (J. Compton, et al., Nature, 350, 91-92, 1991), strand displacement amplification (SDA) (G. T. Walker, et. al., Proc. Natl. Acad. Sci USA, 89, 392-396, 1992), self-sustained sequence replication (3SR) (J. C. Guatelli, et al., Proc Natl. Acad. Sci. USA, 87, 1874-1878, 1990), transcription-mediated amplification (TMA) (JP Patent No. 3241717), and Qβ replicase amplification (JP Patent No. 2710159). In these isothermal nucleic acid amplification techniques, primer elongation and primer annealing to a single-strand elongation product are carried out in a reaction mixture that is maintained at a constant temperature.

Among these techniques, TMA, Qβ replicase amplification, 3SR, and NASBA techniques, whereby RNA is amplified in the end, involve the use of RNA polymerase or reverse transcriptase to amplify the target nucleic acid sequence in a sample. Since these techniques do not comprise a high temperature cycle for accelerating denaturation during the reaction, a template has a secondary structure and thus annealing of a primer to the template may not be satisfactorily carried out. Thus, these techniques cannot always produce an amplified product even with the use of a primer that can yield an amplified product of interest by PCR. For the same reason, it is difficult to detect an amplified product of a sequence to be detected. Even though primer and probe sequences were designed at regions of interest, therefore, amplification or detection efficiency is not always satisfactory, and designing of the primers or probes that could be employed for isothermal amplification was difficult. As is apparent from the foregoing explanation, conventional isothermal amplification techniques have various drawbacks such as the difficulty of designing primers and probes that could effectively produce and detect amplified products with high sensitivity. Therefore, development of a technique of isothermal nucleic acid amplification has been awaited in order to overcome such drawbacks.

DISCLOSURE OF THE INVENTION

A primary object of the present invention is to provide a method that allows rapid and highly sensitive gene expression analysis or quantification thereof via a simple procedure, which overcomes the drawbacks of conventional isothermal amplification techniques.

The present inventors introduced a template-nonspecific sequence into the target gene and invented a method of rapid and highly sensitive nucleic acid detection that utilizes the isothermal amplification and detection of aforementioned template-specific sequences.

Specifically, the present invention provides a method for detecting a target nucleic acid comprising the following steps, which comprises detecting a sequence that is nonspecific to the target nucleic acid in the transcription product:

step 1 of subjecting the target nucleic acid as a template to reverse transcription using the first primer comprising the first base sequence complementary to sequence F1 of the target nucleic acid, the second base sequence complementary to a promoter sequence of RNA polymerase, and an arbitrary third base sequence, in that order from the 3' end;

step 2 of subjecting the target nucleic acid as a template to digestion with an enzyme;

step 3 of subjecting the reverse transcription product as a template to elongation using the second primer comprising the fourth base sequence identical to sequence F2 located at a position closer to the 5' end than the sequence F1 of the target nucleic acid; and step 4 of subjecting the elongation product to transcription with RNA polymerase.

In the second embodiment, the first primer further comprises at its 5' end the fifth base sequence identical to a promoter sequence of RNA polymerase, and the detection method according to the second embodiment further comprises:

step 5 of subjecting a transcription product comprising a sequence complementary to the fourth base sequence obtained in step 4, the first base sequence, the second base sequence, and the third base sequence as a template to reverse transcription using the second primer;

step 6 of subjecting the elongation product as a template to digestion with an enzyme;

step 7 of subjecting the reverse transcription product as a template to elongation using the first primer; and step 8 of subjecting the elongation product to transcription with RNA polymerase.

In the third embodiment, the first primer further comprises at its 5' end an arbitrary sixth base sequence, and the detection method according to the third embodiment further comprises:

step 4 of subjecting the elongation product obtained in step 3 to transcription with RNA polymerase and subjecting the third primer comprising a sequence identical to the sixth base sequence to elongation with the DNA polymerase with strand displacement activity;

step 5 of synthesizing a double-strand nucleic acid from the elongation product of the third primer as a template using the second primer; and step 6 of subjecting the double-strand nucleic acid to transcription with RNA polymerase and to nucleic acid synthesis using the third primer and DNA polymerase with strand displacement activity.

In the method according to the present invention, a sequence nonspecific to the target nucleic acid in the transcription product comprises a sequence complementary to the third base sequence. According to the third embodiment, particularly, a sequence nonspecific to the target nucleic acid in the transcription product comprises sequences complementary to the third base sequence and to the fifth base sequence.

According to the present invention, the target gene can be detected by detecting a sequence complementary to the third base sequence in the transcription product. For example, a probe comprising the third base sequence and having at its ends a fluorophore and a quencher bound thereto is allowed to hybridize to the transcription product, and light emitted from the fluorophore is detected. Thus, the target gene can be detected.

In order to detect the target gene more rapidly, a primer is preferably designed to bring the number of bases constituting the transcription product to 20 to 61.

In the nucleic acid detection method according to the present invention, the temperature cycle required for PCR is not necessary. Therefore, nucleic acid detection can be carried out more rapidly with higher sensitivity with the use of a simple apparatus.

According to the present invention, amplified product sequences can be shortened. This can shorten the time required for RNA amplification and the time required for amplification of a larger quantity of RNA, compared with the prior art of isothermal nucleic acid amplification. Since the sequence of the amplified product can be designed in view of detection efficiency regardless of the template sequence, probe design is not complicated, and detection can be carried out with high sensitivity.

PREFERRED EMBODIMENTS OF THE INVENTION

In the present invention, a sequence complementary to a promoter sequence of RNA polymerase is used as a primer for isothermal amplification, and a tag sequence is added to the 5' end thereof. Thus, the target nucleic acid is subjected to reverse transcription using the aforementioned primer, a promoter sequence is generated upon conversion of the sequence into double-strand DNA, and a sequence complementary to the tag sequence is obtained as a transcription product. According to the method of the present invention, a tag sequence unrelated to the target nucleic acid sequence is amplified instead of the target nucleic acid, and the tag sequence in the amplified product is detected. Thus, a gene can be detected rapidly with high sensitivity.

Figure 1:
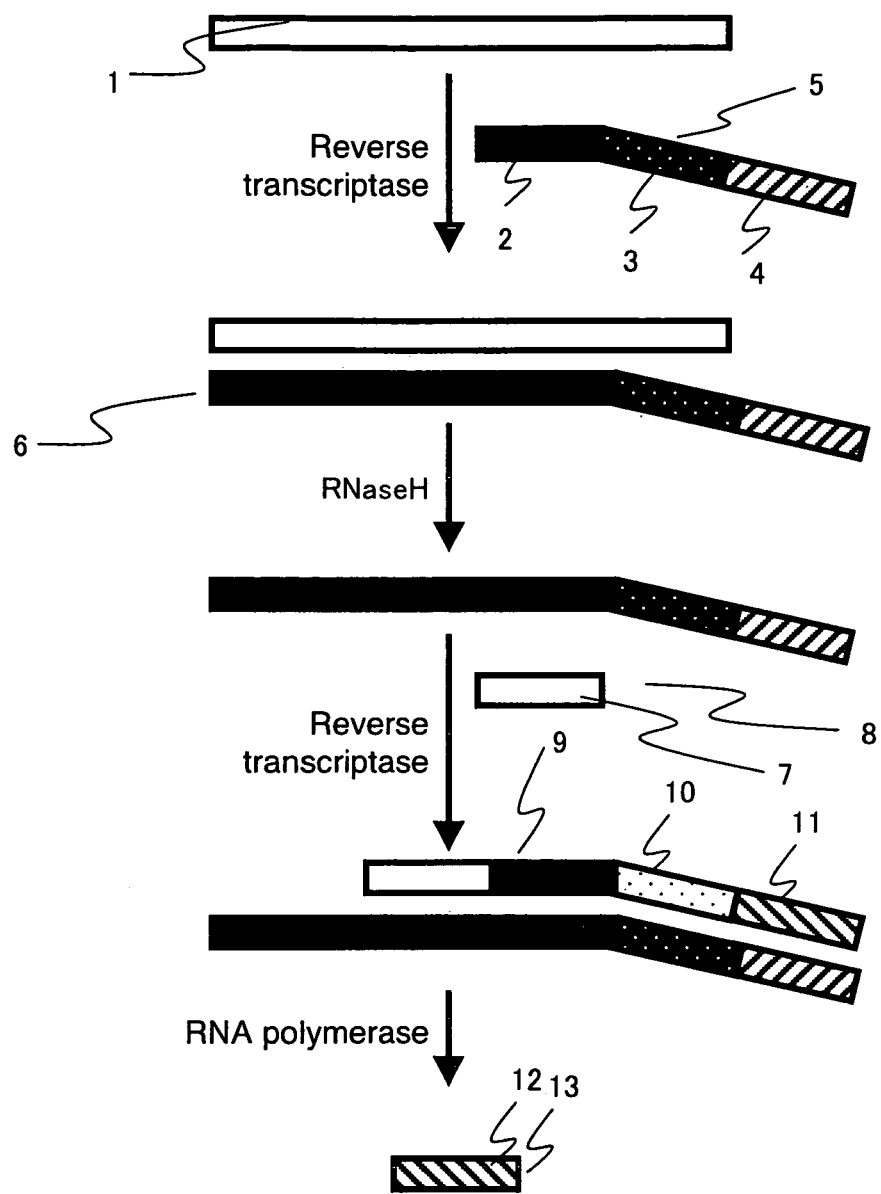
FIG. 1 shows the procedure according to the first embodiment of the present invention.

FIG. 1 shows the procedure according to the first embodiment of the present invention. The present invention relates to a method for amplifying and detecting a nucleic acid sequence. This method comprises: step 1 of subjecting the template target gene 1 to reverse transcription using a P1 primer 5 comprising a base sequence 2 having a sequence specific to the base sequence of the target gene 1, a base sequence 3 complementary to a promoter sequence of RNA polymerase, and an arbitrary base sequence 4; step 2 of subjecting the template of the product obtained in step 1, i.e., the target gene 1, to digestion; step 3 of subjecting the P2 primer 8 comprising a base sequence 7 specific to the base sequence of the target gene to elongation with a reverse transcriptase using a reverse transcription product 6, which has been single-stranded via step 2, as a template; step 4 of subjecting double-strand DNA comprising the elongation product 9 obtained in step 3 to transcription as a template using RNA polymerase recognizing a promoter sequence 10 of RNA polymerase; and step 5 of detecting a transcription product 13 comprising a sequence 12 complementary to the base sequence 4.

Figure 2:
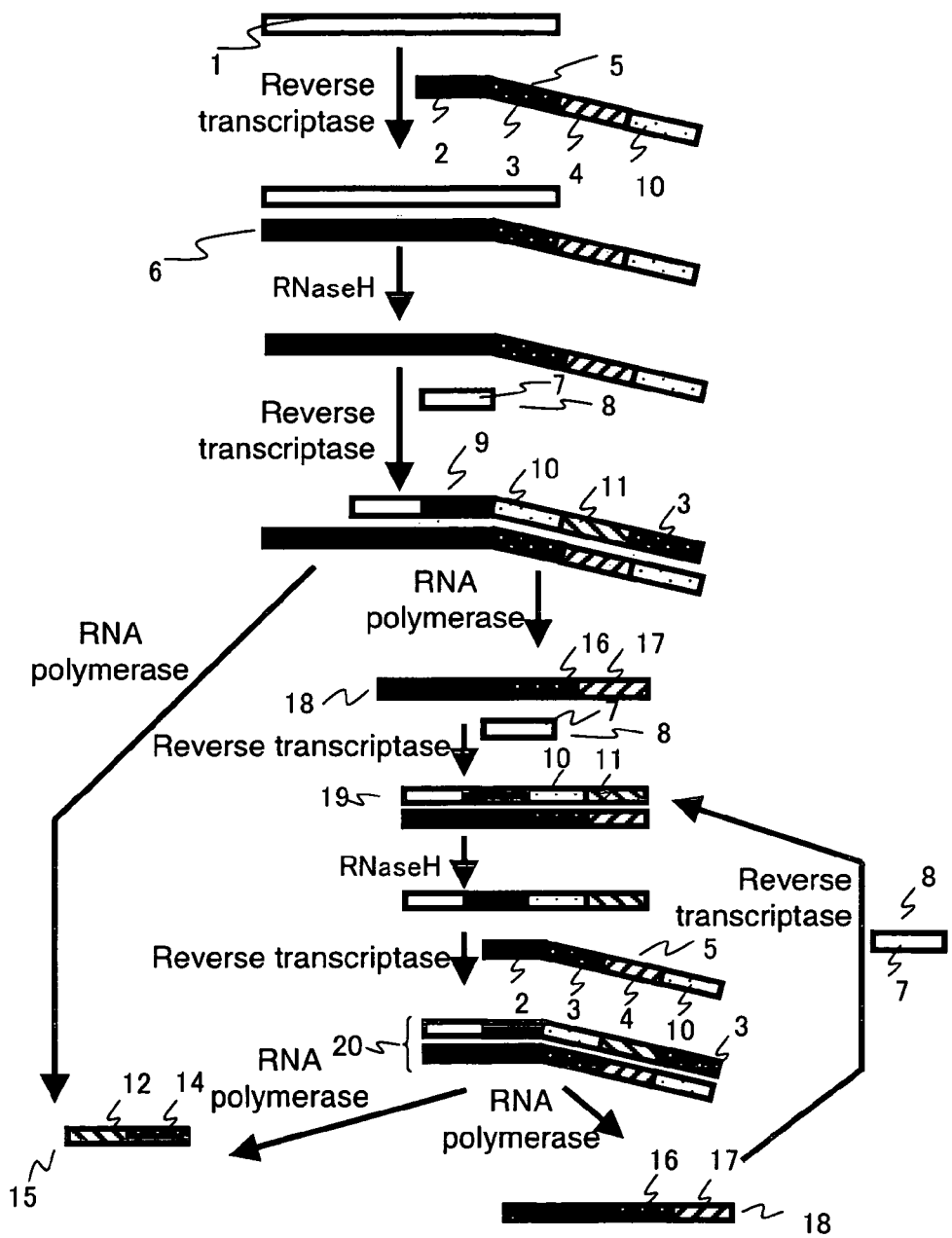
FIG. 2 shows the procedure according to the second embodiment of the present invention.

FIG. 2 shows the procedure according to the second embodiment of the present invention. The present invention relates to a method for amplifying a nucleic acid sequence. This method comprises: step 1 of subjecting the template target gene 1 to reverse transcription using the P1 primer 5, which further comprises a base sequence 10 that is a promoter sequence of RNA polymerase at the 5' end of the primer comprising a base sequence 2 having a sequence specific to the base sequence of the target gene 1, a base sequence 3 complementary to a promoter sequence of RNA polymerase, and an arbitrary base sequence 4; step 2 of subjecting the template of the product obtained in step 1, i.e., the target gene 1, to digestion; step 3 of subjecting the P2 primer 8 comprising a base sequence 7 specific to the base sequence of the target gene to elongation with a reverse transcriptase using a template reverse transcription product 6, which has been single-stranded via step 2; step 4 of obtaining a reverse transcription product 15 comprising sequences 12 and 14 complementary to the base sequences 4 and 10 and a transcription product 18 comprising sequences complementary to the base sequences 7, 10, and 11 from the template double-strand DNA comprising the elongation product 9 obtained in step 3 using RNA polymerase; step 6 of subjecting the template transcription product 18 obtained in step 4 to reverse transcription using the P2 primer 8; step 7 of subjecting the transcription product 18 as a template of the product obtained in step 6 to digestion; step 8 of allowing the P1 primer 5 to hybridize to the reverse transcription product 19, which has been single-stranded via step 7, thereby elongating both the primer and the reverse transcription product using a reverse transcriptase; step 9 of subjecting the template double-strand DNA 20 obtained via step 8 to transcription with RNA polymerase; and step 10 of subjecting the template transcription product 18 obtained via step 9 to reverse transcription using the P2 primer 8 to resynthesize the reverse transcription product 19 generated via step 6. Also, the method detects a transcription product 15 amplified by repeating steps 6, 7, 8, 9, and 10.

Figure 3:
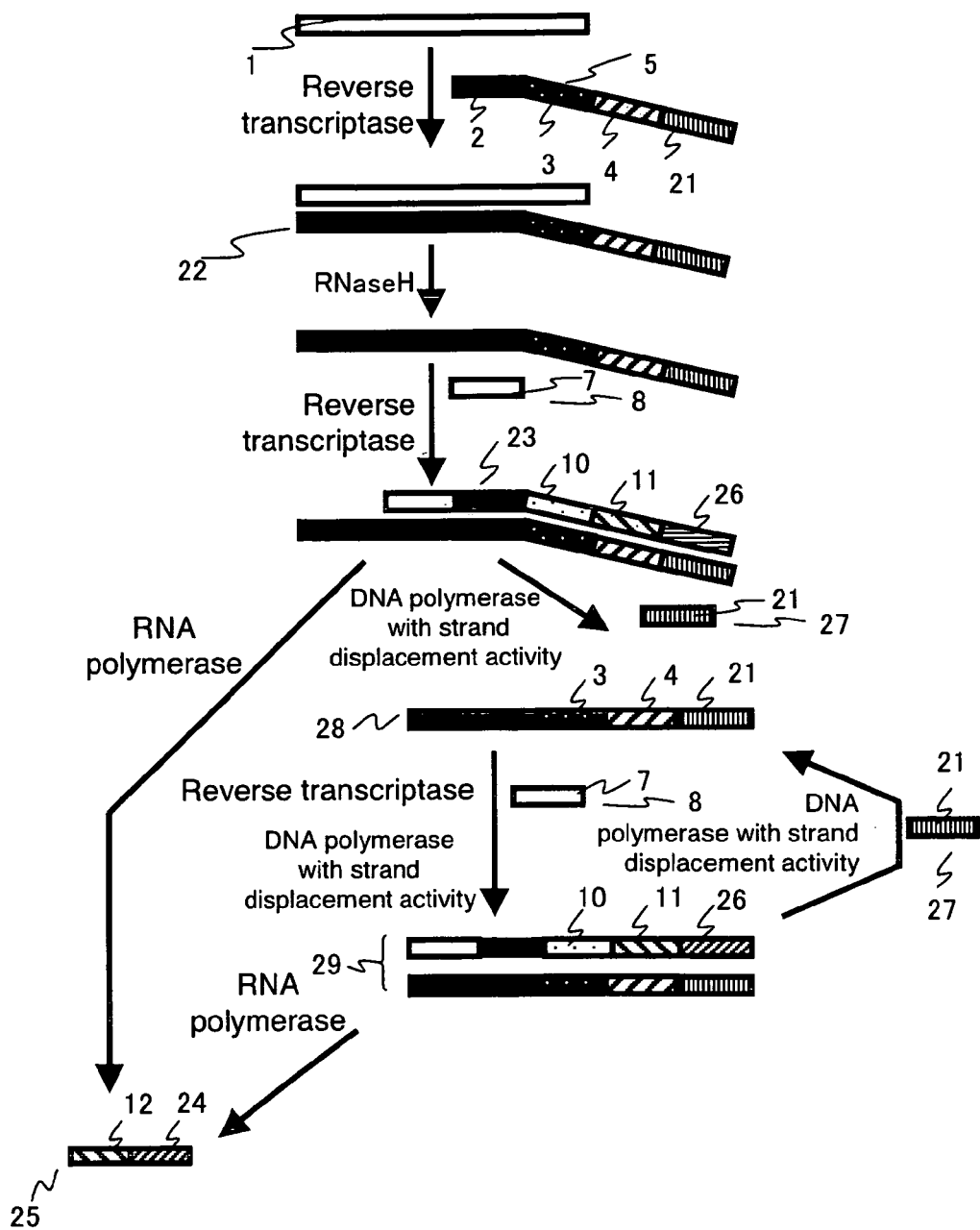
FIG. 3 shows the procedure according to the third embodiment of the present invention.

FIG. 3 shows the procedure according to the third embodiment of the present invention. The present invention relates to a method for amplifying a nucleic acid sequence to detect a target gene. This method comprises: step 1 of subjecting the template target gene 1 to reverse transcription using the P1 primer 5, which further comprises an arbitrary base sequence 21 at the 5' end of the primer comprising a base sequence 2 having a sequence specific to the base sequence of the target gene 1, a base sequence 3 complementary to a promoter sequence of RNA polymerase, and an arbitrary base sequence 4; step 2 of subjecting the template of the product obtained in step 1, i.e., the target gene 1, to digestion; step 3 of subjecting the P2 primer 8 comprising a base sequence 7 having a sequence specific to the base sequence of the target gene to elongation with a reverse transcriptase using a reverse transcription product 22, which has been single-stranded via step 2, as a template; step 6 of obtaining a transcription product 25 comprising sequences 12 and 24 complementary to the base sequences 4 and 21 from the template double-strand DNA comprising the elongation product 23 obtained in step 3 using RNA polymerase and obtaining an elongation product 28 comprising sequences complementary to the base sequences 7, 10, 11, and 26 from the template double-strand DNA comprising the elongation product 23 obtained in step 3 using a primer 27 having an arbitrary sequence 21 and the strand displacement RNA polymerase; step 7 of subjecting the template elongation product 28 obtained via step 6 to elongation using the P2 primer 8; step 8 of obtaining a transcription product 25 comprising sequences 12 and 24 complementary to the base sequences 4 and 21 from the template double-strand DNA 29 obtained via step 7 using RNA polymerase; step 9 of obtaining an elongation product 28 comprising sequences complementary to the base sequences 7, 10, 11, and 26 from the template double-strand DNA 29 obtained via step 7 using a primer 27 having an arbitrary sequence 21 and DNA polymerase with strand displacement activity; and step 10 of resynthesizing double-strand DNA by allowing the P2 primer 8 to elongate from the template elongation product 28 obtained via step 9. In the method for amplifying a nucleic acid sequence according to the present invention, the amplified transcription product 25 is detected by repeating steps 7, 8, 9, and 10.

According to the procedure of the second embodiment of the present invention, a transcription product 15, which comprises a sequence unrelated to the target gene that had been introduced into the 5' end of the target gene (i.e., the sequences 12 and 14 complementary to the base sequences 4 and 10), is amplified and then detected.

According to the procedures of the first, the second, and the third embodiments of the present invention, a nucleic acid can be detected by allowing a probe having a sequence complementary to the base sequence 4 included in the P1 primer and having at its ends a fluorophre and a quencher bound thereto to hybridize to the transcription product 13 (via the procedure of the first embodiment), the transcription product 15 (via the procedure of the second embodiment), or a transcription product 25 and an elongation product 28 (via the procedure of the third embodiment), and detecting the light emitted from the fluorophore in step 5. Alternatively, nucleic acids amplified products can be detected via electrophoresis.

In the method of the present invention, a temperature cycle may be employed, and a template nucleic acid sequence may be an RNA sequence or DNA sequence. Also, template DNA may be single-strand DNA or double-strand DNA. When double-strand DNA is used as a template, the method of the present invention should be carried out following a process of pretreatment, so as to denature the double-strand DNA into single-strand DNA.

EXAMPLES

The present invention is hereafter described in greater detail with reference to the examples, although the technical scope of the present invention is not limited to these examples.

Example 1

1. Oligonucleotide Primers Used in Example 1

```
P1 primer 1:                                  (SEQ ID NO: 1)
5'-CCCTTCTCACTGTTCTCTCATTCTCCCTATAGTGAGTCGTATTAGAAT
TCTCGCAAGCACCCTATCAGGCAGT-3'

P2 primer 2:                                  (SEQ ID NO: 2)
5'-GCAGAAAGCGTCTAGCCATGGCGT-3'
```

2. Molecular Beacon Probe Used in Example 1

```
MBPa:                                         (SEQ ID NO: 3)
5'-CGACGTCCCTTCTCACTGTTCTCTCATACGTCG-3'
```

The amplified product was detected via molecular beacon probe-based real-time PCR assay in order to determine whether or not the gene expression analysis could be carried out in accordance with the procedure according to the first embodiment of the present invention.

RNA of hepatitis C virus (HCV) genotype II was used as a template (concentration: $1.8 \times 10^2$ μg/ml), and the primers described in 1 above were used as the oligonucleotide primers for amplification. The P1 primer 1 was a reverse primer consisting of: a sequence between positions 1 and 21 from the 5' end where MBPa hybridized to the amplified product; a sequence between positions 22 and 49 complementary to a promoter sequence of T7 RNA polymerase; and a sequence between positions 50 and 73 specific to RNA of HCV genotype II. The P2 primer 2 was a forward primer consisting of a sequence specific to RNA of HCV genotype II. The MBPa described in 2 above was used as a detection probe. MBPa was labeled at its 5' end with FAM and at its 3' end with BHQ1, a sequence between positions 1 and 6 and a sequence between positions 28 and 33 from the 5' end were stem sequences, and a sequence between positions 7 and 27 hybridized to an amplified product.

The commercially available NucliSens® Basic kit (bioMerieux) was used, and a reaction solution for amplification was prepared in accordance with the manufacturer's instructions.

Figure 4:
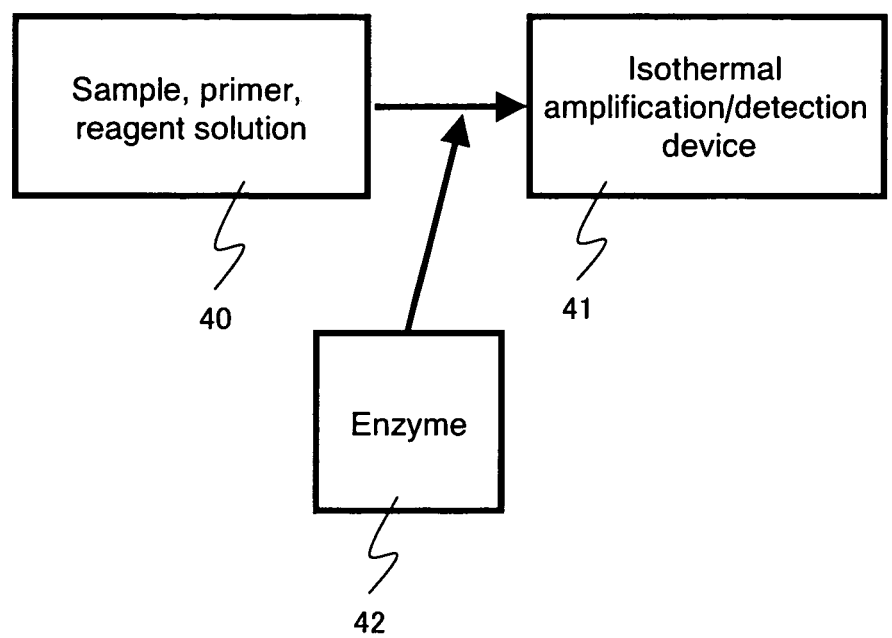
FIG. 4 shows the procedure of real-time detection according to the present invention.
Figure 5:
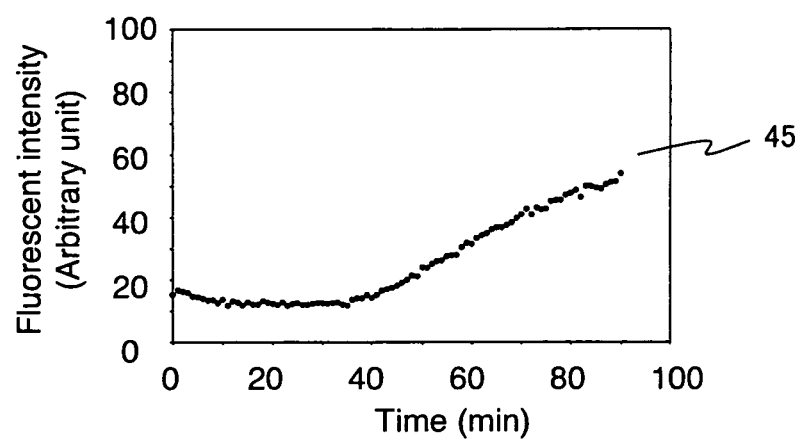
FIG. 5 shows the results of analyzing the amplified product via electrophoresis, obtained by the procedure according to the first embodiment of the present invention wherein RNA of HCV genotype II was used as a template.

FIG. 4 shows a procedure for real-time detection according to the present invention. An enzyme 42 was added to a reaction solution 40 comprising a sample RNA, a primer, a reagent, and the like, amplification was carried out using an isothermal amplification/detection apparatus 41, and the amplified product was detected via real-time PCR. A Corona fluorescence microplate reader (Corona Electric Co., Ltd.) was used as the isothernal amplification/detection apparatus 41. FIG. 5 is a graph (numeral reference 45) showing the results of real-time detection in accordance with the procedure of the first embodiment of the present invention. The vertical axis represents the fluorescence intensity of FAM, the horizontal axis represents the time, and the curve represents changes in the fluorescence intensity of the amplified product of the sample RNA in accordance with the duration of the reaction time. The fluorescence intensity of FAM determined via real-time detection increased with the elapse of time. This indicates that the amplified product was detected via the procedure according to the first embodiment of the present invention. Further, such results of detection support the fact that gene expression analysis can be carried out in accordance with the procedure according to the third embodiment of the present invention.

Example 2

1. Oligonucleotide Primers Used in Example 2

```
P1 primer 3:                            (SEQ ID NO: 4)
5'-ATTTAGGTGACACTATAGAATACCACTCATCTCTTCTCCCTGTTTCTC
CCTATAGTGAGTCGTATTAGAATTCAAGCACCCTATCAGGCAGTA-3'

P2 primer 4:                            (SEQ ID NO: 5)
5'-GTCTAGCCATGGCGTTAGTA-3'
```

2. Molecular Beacon Probe Used in Example 2

```
MBPb:                                   (SEQ ID NO: 6)
5'-CGACGTCACTCATCTCTTCTCCCTGTTACGTCG-3'
```

The reaction product was analyzed via electrophoresis in order to determine that the procedure of the second embodiment of the present invention could yield an amplified product of interest.

RNA of hepatitis C virus (HCV) genotype II was used as a template (concentration: $1.8 \times 10^2$ µg/ml), and the primers described in 1 above were used as the oligonucleotide primers for amplification. The P1 primer 3 was a reverse primer consisting of: a sequence between positions 1 and 23 from the 5' end, which is a promoter sequence of SP6 RNA polymerase; a sequence between positions 24 and 44 where MBPb hybridized to the amplified product; a sequence between positions 45 and 72 complementary to a promoter sequence of T7 RNA polymerase; and a sequence between positions 73 and 93 specific to RNA of HCV genotype II. The P2 primer 4 was a forward primer consisting of a sequence specific to RNA of HCV genotype II. The MBPb described in 2 above was used as a detection probe. MBPb was labeled at its 5' end with FAM and at its 3, end with BHQ1, a sequence between positions 1 to 6 and a sequence between positions 28 to 33 from the 5' end were stem sequences, and a sequence between positions 7 to 27 hybridized to an amplified product.

The commercially available NASBA amplification kit (Kainos) was used, a reaction solution was prepared in accordance with the manufacturer's instructions, SP6 RNA polymerase was added thereto, and the resulting mixture was used for amplification.

Figure 6:
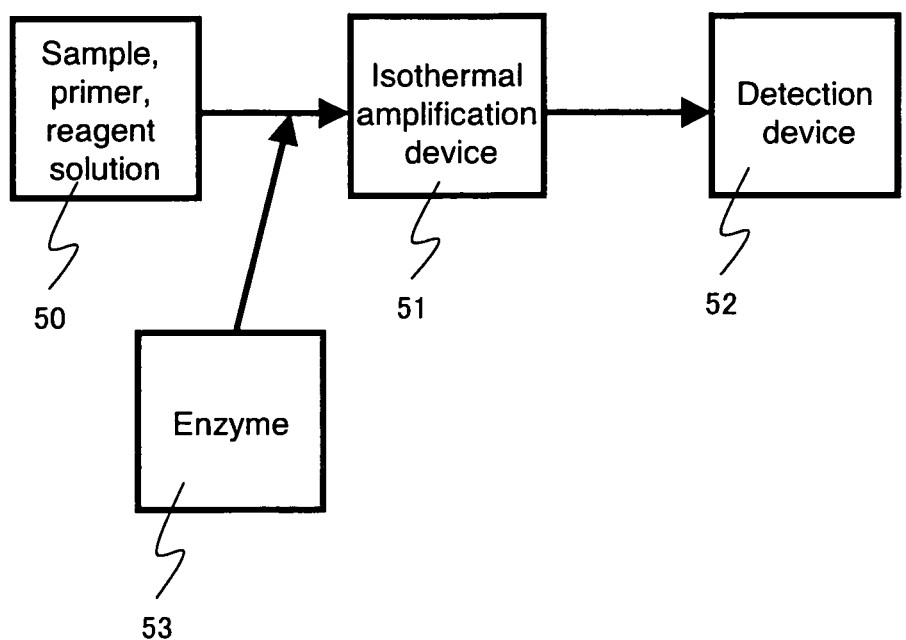
FIG. 6 shows the procedure of amplification according to the method of the present invention.
Figure 7:
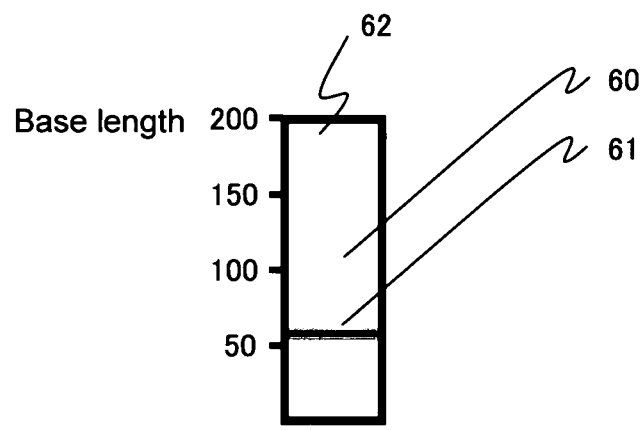
FIG. 7 shows the results of analyzing the amplified product via electrophoresis, obtained by the procedure according to the second embodiment of the present invention wherein RNA of HCV genotype II was used as a template.

FIG. 6 shows a procedure for amplification according to the present invention. A reaction solution 50 comprises a sample RNA, a primer, a reagent, and the like. The reaction solution was incubated at 65° C. for 5 minutes and then at 41° C. for 5 minutes, an enzyme 53 was then added thereto, the reaction was carried out in an isothermal amplification apparatus 51 at 41° C. for 90 minutes, and the resulting reaction product was detected using a detection apparatus 52. Cosmo-i SV1210 (Hitachi High-Technologies Corp.) was used as the detection apparatus 52. FIG. 7 is an image (a numerical reference 62) showing the results of electrophoresis on Cosmo-i SV1210 in Example 2. As shown in FIG. 7, a 52-base-long amplified product 60 of RNA detected with the use of MBPb and an amplified product 61 of RNA used as a template in the amplification procedure were observed. This indicates that the amplified product of interest could be obtained and the target gene could be detected in accordance with the procedure of the second embodiment of the present invention.

Example 3

1. Oligonucleotide Primers Used in Example 3

```
P1 primer 5:                            (SEQ ID NO: 7)
5'-ATTTAGGTGACACTATAGAATACCTCTGTTCCCTCATCACTTCTTCTC
CCTATAGTGAGTCGTATTAGAATTCAAGCACCCTATCAGGCAGTA-3'

P2 primer 4:                            (SEQ ID NO: 5)
5'-GTCTAGCCATGGCGTTAGTA-3'
```

2. Molecular Beacon Probe Used in Example 3

```
MBPc:                                   (SEQ ID NO: 8)
5'-CGACGTCTCTGTTCCCTCATCACTTCTACGTCG-3'
```

The amplified product was detected via molecular beacon probe-based real-time PCR assay in order to determine whether or not the gene expression levels could be analyzed using the data obtained in accordance with the procedure of the second embodiment of the present invention.

RNAs of hepatitis C virus (HCV) genotype II serially diluted in 10-fold increments (concentrations: $1.8 \times 10^3$ µg/ml, $1.8 \times 10^2$ µg/ml, $1.8 \times 10^1$ µg/ml, $1.8 \times 10^0$ µg/ml, and $1.8 \times 10^{-1}$ µg/ml) were used as templates, and the primers described in 1 above were used as the oligonucleotide primers for amplification. The P1 primer 5 was a reverse primer consisting of: a sequence between positions 1 and 23 from the 5' end, which is a promoter sequence of SP6 RNA polymerase; a sequence between positions 24 and 44 where MBPc hybridized to the amplified product; a sequence between positions 45 and 72 complementary to a promoter sequence of T7 RNA polymerase; and a sequence between positions 73 and 93 specific to RNA of HCV genotype II. The P2 primer 4 was a forward primer having a sequence specific to RNA of HCV genotype II. The MBPc described in 2 above was used as a detection probe. MBPc was labeled at its 5' end with FAM and at its 3, end with BHQ1, a sequence between positions 1 to 6 and a sequence between positions 28 to 33 from the 5' end were stem sequences, and a sequence between positions 7 to 27 hybridized with an amplified product.

The commercially available NucliSens® Basic kit (bioMerieux) was used, and a reaction solution was prepared in accordance with the manufacturer's instructions, SP6 RNA polymerase was added thereto, and the resulting mixture was used for amplification.

FIG. 4 shows a procedure for real-time detection according to the present invention. An enzyme 42 was added to a reaction solution 40 comprising a sample RNA, a primer, a reagent, and the like, amplification was carried out using an isothermal amplification/detection apparatus 41, and the amplified product was detected via real-time PCR. A Corona fluorescence microplate reader (Corona Electric Co., Ltd.) was used as the isothernal amplification/detection apparatus 41.

Figure 8:
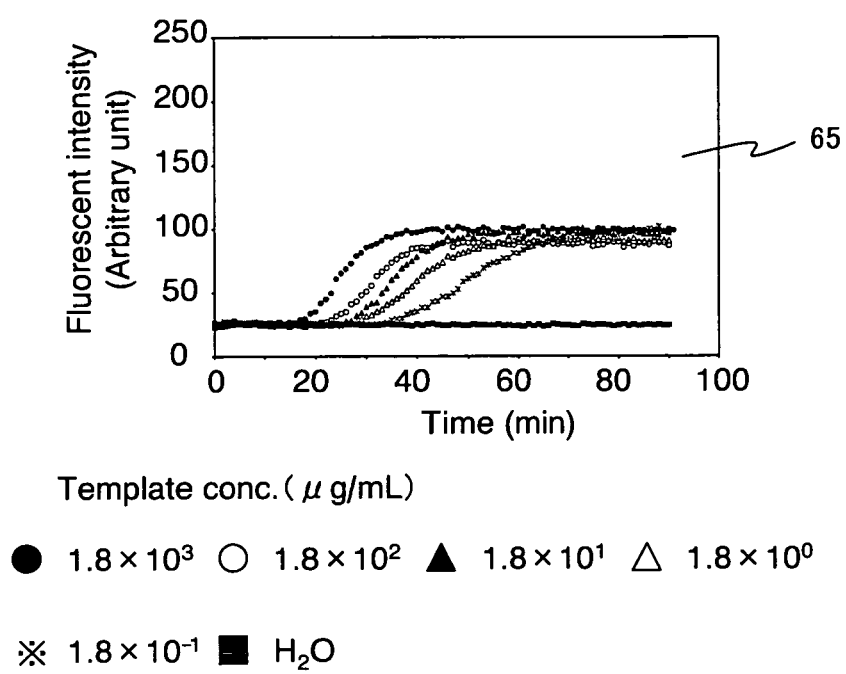
FIG. 8 shows the results of real-time detection of the amplified product, obtained via the procedure of the second embodiment of the present invention wherein RNA of HCV genotype II was used as a template.

FIG. 8 is a graph (numeral reference 65) showing the results of real-time detection in accordance with the procedure of the second embodiment of the present invention. The vertical axis represents the fluorescence intensity of FAM, the horizontal axis represents the time, and the curve represents changes in the fluorescence intensity of the amplified product of the sample RNA in accordance with the duration of the reaction time. The black circle, white circle, black triangle, white triangle, and reference mark each represent a concentration of template used for amplification ($1.8 \times 10^3$ μg/ml, $1.8 \times 10^2$ μg/ml, $1.8 \times 10^1$ μg/ml, $1.8 \times 10^0$ μg/ml, and $1.8 \times 10^{-1}$ μg/ml, in that order), and the black square represents the results of detection wherein water was used instead of a template as a negative control. The fluorescence intensities of FAM obtained with the template concentrations represented by the black circle, white circle, black triangle, white triangle, and reference mark increased with the elapse of time. In contrast, the fluorescence intensities were maintained at a constant level when water was used instead of the template represented by the black square as a negative control. This indicates that an amplified product can be detected via real-time PCR in accordance with the procedure according to the second embodiment of the present invention. Since the time points at which the curves rise vary in accordance with the template concentration, it was confirmed that the gene expression levels were quantified by analyzing the results obtained above.

Example 4

1. Oligonucleotide Primers Used in Example 4

```
P1 primer 6:                              (SEQ ID NO: 9)
5'-ATTTAGGTGACACTATAGAATACCCCTTCTCTCTCATCACTGTTTCTC
CCTATAGTGAGTCGTATTAGAATTTAGTTGCAGTAGTTCTCCAG-3'

P2 primer 7:                             (SEQ ID NO: 10)
5'-TGGTGCAGGCAGCCTGCA-3'
```

2. Molecular Beacon Probe Used in Example 4

```
MBPd:                                    (SEQ ID NO: 11)
5'-CGACGTCCCTTCTCTCTCATCACTGTTACGTCG-3'
```

3. Composition of the Reaction Solution Used in Example 4 (Values in Parentheses are the Final Concentrations)

Tris-HCl pH 8.5 (40 mM), $MgCl_2$ (12 mM), KCl (70 mM), DTT (0.5 mM), dNTP (1.0 mM), ATP (2.0 mM), CTP (2.0 mM), UTP (2.0 mM), GTP (1.5 mM), and ITP in 30% DMSO (0.5 mM)

4. Composition of the Enzyme Used in Example 4

2.1 μg of BSA, 0.08 U of RNaseH, 32 U of T7 RNA polymerase, 6.4 U of AMV reverse transcriptase, 25 U of SP6 RNA polymerase, and 16 U of Bst DNA polymerase The amplified product was detected via molecular beacon probe-based real-time PCR assay in order to determine whether or not the gene expression analysis could be carried out in accordance with the procedure according to the third embodiment of the present invention.

The template used was the insulin gene (concentration: $5.0 \times 10^2$ μg/ml), and the primers described in 1 above were used as the oligonucleotide primers for amplification. The P1 primer 6 was a reverse primer consisting of: a sequence between positions 1 and 23 from the 5' end, which is a promoter sequence of SP6 RNA polymerase; a sequence between positions 24 and 44 where MBPd hybridized to the amplified product; a sequence between positions 45 and 72 complementary to a promoter sequence of T7 RNA polymerase; and a sequence between positions 73 and 93 specific to the A chain region of the insulin gene. The P2 primer 7 was a forward primer consisting of a sequence specific to the A chain domain of the insulin gene. The detection probe used was MBPd described in 2 above. MBPd was labeled at its 5' end with FAM and at its 3' end with BHQ1, a sequence between positions 1 and 6 and a sequence between positions 28 and 33 from the 5' end were stem sequences, and a sequence between positions 7 and 27 was a sequence hybridizing to the amplified product.

Figure 9:
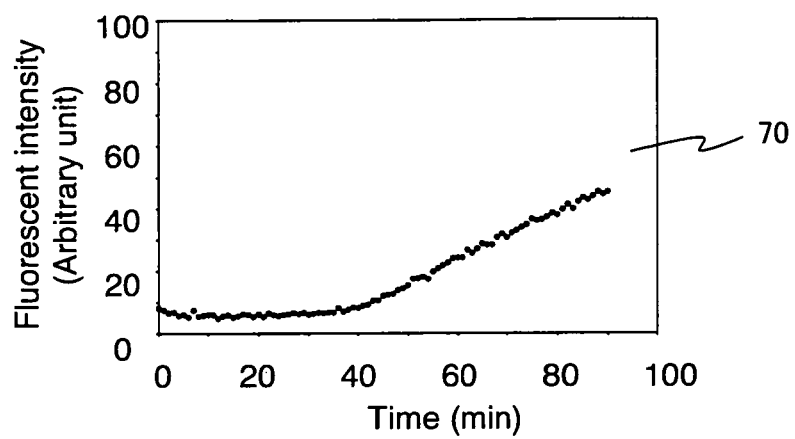
FIG. 9 shows the results of real-time detection of the amplified product, obtained via the procedure of the third embodiment of the present invention wherein the insulin gene was used as a template.

FIG. 4 shows the procedure of real-time detection according to the present invention. The composition of the reaction solution for amplification and the composition of the enzyme according to the present invention were specifically described in 3 and 4 above. An enzyme 42 was added to a reaction solution 40 comprising a sample RNA, a primer, a reagent, and the like, amplification was carried out using an isothermal amplification/detection apparatus 41, and the amplified product was detected via real-time PCR. A Corona fluorescence microplate reader (Corona Electric Co., Ltd.) was used as the isothernal amplification/detection apparatus 41. FIG. 9 is a graph (numeral reference 70) showing the results of real-time detection. The vertical axis represents the fluorescence intensity of FAM, the horizontal axis represents the time, and the curve represents changes in the fluorescence intensity of the amplified product of the sample RNA in accordance with the duration of the reaction time. The fluorescence intensity of FAM determined via real-time detection increased with the elapse of time. This indicates that the amplified product was detected via the procedure according to the third embodiment of the present invention. Accordingly, it was confirmed that gene expression analysis could be carried out in accordance with the procedure according to the third embodiment of the present invention.

Example 5

1. Oligonucleotide Primers Used in Example 5

```
P1 primer 8:                              (SEQ ID NO: 12)
5'-ATTTAGGTGACACTATAGAATACCACTCATCCCTGTTCTCTTCTTCT
CCCTATAGTGAGTCGTATTAGAATTGTTTGCAGCTCTGTGCATA-3'

P1 primer 9:                              (SEQ ID NO: 13)
5'-AATTCTAATACGACTCACTATAGGGAGAGTTTGCAGCTCTGTGCA
TA-3'

P2 primer 10:                             (SEQ ID NO: 14)
5'-AAGGGCGTAACCGAAATCGG-3'

P2 primer 11:                             (SEQ ID NO: 15)
5'-CACTCATCCCTGTTCTCTTCTAAGGGCGTAACCGAAATCGG-3'
```

2. Molecular Beacon Probe Used in Example 5

```
MBPe:                                     (SEQ ID NO: 16)
5'-CGACGTCACTCATCCCTGTTCTCTTCTACGTCG-3'
```

In order to determine whether or not the method of the present invention could implement amplification and detection within a time frame shorter than that of the prior art, molecular beacon probe-based real-time PCR assays were carried out in accordance with the procedure according to the second embodiment of the present invention and via the prior art, and the results were compared.

The double-strand DNA of the human papillomavirus (HPV) was used as the template. The P1 primer 8 and the P2 primer 10 described in 1 above were used as the oligonucleotide primers in the procedure according to the second embodiment of the present invention. The P1 primer 9 and the P2 primer 11 were used as the oligonucleotide primers in a conventional method. The P1 primer 8 was a reverse primer consisting of: a sequence between positions 1 and 23 from the 5' end, which is a promoter sequence of SP6 RNA polymerase; a sequence between positions 24 and 44 where MBPe hybridized to the amplified product; a sequence between positions 45 and 72 complementary to a promoter sequence of T7 RNA polymerase; and a sequence between positions 73 and 93 specific to human papillomavirus. The P1 primer 9 was a reverse primer consisting of a sequence between positions 1 and 28 from the 5' end, which is a promoter sequence of T7 RNA polymerase, and a sequence between positions 29 and 47 specific to human papillomavirus. The P2 primer 10 was a forward primer consisting of a sequence specific to human papillomavirus. The P2 primer 11 was a forward primer consisting of a sequence between positions 1 and 21 from the 5' end where MBPe hybridized to the amplified product, and a sequence between positions 29 and 41 specific to human papillomavirus. The detection probe used was MBPe described in 2 above. MBPe was labeled at its 5' end with FAM and at its 3' end with BHQ1, a sequence between positions 1 and 6 and a sequence between positions 28 and 33 from the 5' end were stem sequences, and a sequence between positions 7 and 27 was a sequence hybridizing to the amplified product.

A specific example of the composition of the reaction solution according to the method of the present invention is a mixture of the commercially available NASBA amplification kit (Kainos) and SP6 RNA polymerase.

Figure 10:
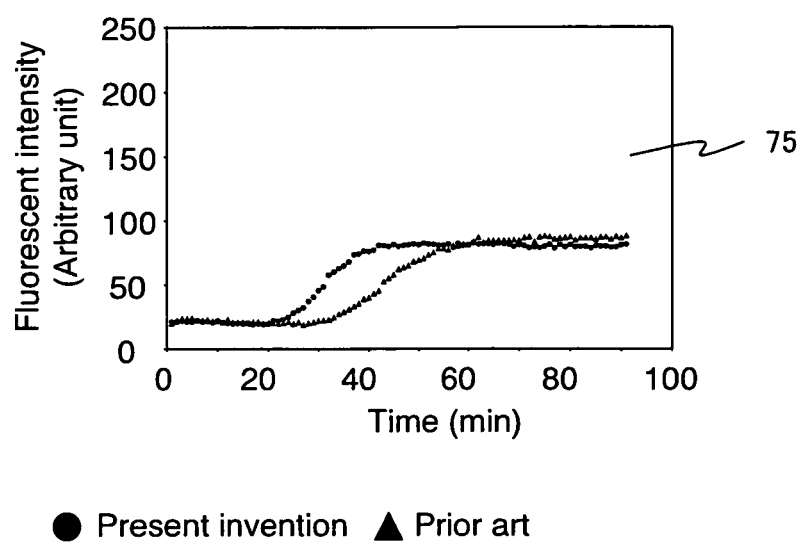
FIG. 10 shows the results of real-time detection of the amplified products, obtained by the procedure according to the second embodiment of the present invention and by a method of the prior art wherein human papillomavirus was used as a template.

FIG. 4 shows a procedure for real-time detection according to the present invention. An enzyme 42 was added to a reaction solution 40 comprising a sample RNA, a primer, a reagent, and the like, amplification was carried out using an isothermal amplification/detection apparatus 41, and the amplified product was detected via real-time PCR. A Corona fluorescence microplate reader (Corona Electric Co., Ltd.) was used as the isothernal amplification/detection apparatus 41. FIG. 10 is a graph (numeral reference 75) showing the results of real-time detection in accordance with the procedure of the second embodiment of the present invention. The vertical axis represents the fluorescence intensity of FAM, the horizontal axis represents the time, and the curve represents changes in the fluorescence intensity of the amplified product of the sample RNA in accordance with the duration of the reaction time. Black circles constitute the curve showing the amount of the amplification product obtained via the procedure according to the second embodiment of the present invention. Back triangles constitute the curve showing the amount of the amplification product obtained via a prior art. The fluorescent intensities of FAM represented by the black circles and by the black triangles increased with the elapse of time; however, the point in time at which the curve rose was approximately 15 minutes earlier with the method according to the present invention than with that of the prior art, and a plateau was attained approximately 20 minutes earlier with the method of the present invention than with the prior art. This indicates that amplification and detection can be carried out within a shorter period of time with the procedure according to the second embodiment of the present invention than with the prior art.

INDUSTRIAL APPLICABILITY

According to the present invention, a target nucleic acid can be amplified and detected within a short period of time with high sensitivity. The present invention can be applied to an extensive range of fields that require nucleic acid detection, such as basic research, virus inspection, genetic diagnosis, and the like.

SEQUENCE LISTING FREE TEXT

SEQ ID NO: 1—description of an artificial sequence: a reverse DNA primer hybridizing to hepatitis C virus, used in the present invention SEQ ID NO: 2—description of an artificial sequence: a forward DNA primer hybridizing to hepatitis C virus, used in the present invention SEQ ID NO: 3—description of an artificial sequence: a DNA probe for detecting an amplified fragment via real-time PCR SEQ ID NO: 4—description of an artificial sequence: a reverse DNA primer hybridizing to hepatitis C virus, used in the present invention SEQ ID NO: 5—description of an artificial sequence: a forward DNA primer hybridizing to hepatitis C virus, used in the present invention SEQ ID NO: 6—description of an artificial sequence: a DNA probe for detecting an amplified fragment via real-time PCR SEQ ID NO: 7—description of an artificial sequence: a reverse DNA primer hybridizing to hepatitis C virus, used in the present invention SEQ ID NO: 8—description of an artificial sequence: a DNA probe for detecting an amplified fragment via real-time PCR SEQ ID NO: 9—description of an artificial sequence: a reverse DNA primer hybridizing to the A chain domain of the insulin gene, used in the present invention SEQ ID NO: 10—description of an artificial sequence: a forward DNA primer hybridizing to the A chain domain of the insulin gene, used in a prior art SEQ ID NO: 11—description of an artificial sequence: a DNA probe for detecting an amplified fragment via real-time PCR SEQ ID NO: 12—description of an artificial sequence: a reverse DNA primer hybridizing to papillomavirus, used in the present invention SEQ ID NO: 13—description of an artificial sequence: a reverse DNA primer hybridizing to papillomavirus, used in a prior art SEQ ID NO: 14—description of an artificial sequence: a forward DNA primer hybridizing to papillomavirus, used in the present invention SEQ ID NO: 15—description of an artificial sequence: a forward DNA primer hybridizing to papillomavirus, used in a prior art SEQ ID NO: 16—description of an artificial sequence: a DNA probe for detecting an amplified fragment via real-time PCR

The invention claimed is:

1. A method for detecting a target nucleic acid which comprises:

detecting a sequence complementary to an arbitrary third base sequence by a hybridization with a sequence complementary to the third base sequence in a transcription product comprising:

step 1 of subjecting the target nucleic acid as a template to reverse transcription using a first primer comprising a first base sequence complementary to a first sequence F1 of the target nucleic acid, a second base sequence complementary to a promoter sequence of RNA polymerase, and the arbitrary third base sequence which can hybridize with a base sequence complementary thereto, wherein the first base sequence, the second base sequence, and the third base sequence are in sequential order from the 3' end of the first primer wherein, the template is a double stranded DNA;

step 2 of subjecting the template of the target nucleic acid obtained in step 1 to digestion with an enzyme;

step 3 of subjecting the reverse transcription product obtained from step 1 as a template to elongation using a second primer comprising a fourth base sequence identical to a second sequence of the target nucleic acid, wherein the second sequence of the target nucleic acid is located at a position closer to the 5' end than the first sequence of the target nucleic acid; and step 4 of subjecting the elongation product obtained from step 3 to transcription with RNA polymerase to produce the transcription product and detecting a base sequence within the transcription product by a hybridization with a probe having the third base sequence, the base sequence detected within the transcription product being complementary to the third base sequence, wherein the sequence complementary to the third base sequence which is transcribed with RNA polymerase by a double-stranded DNA produced from the elongation reaction as a template, and wherein the promoter sequence is a double-stranded DNA constructed the first base sequence and the elongation product.

2. The method for detecting a target nucleic acid according to claim 1, wherein the first primer further comprises at its 5' end a fifth base sequence identical to a promoter sequence of RNA polymerase, which further comprises:

step 5 of subjecting a transcription product obtained from step 4 comprising a sequence complementary to the fourth base sequence, the first base sequence, the second base sequence, and the third base sequence as a template to reverse transcription using the second primer, wherein step 4 produces four transcription products, wherein the first product comprising a complement to a third base sequence and a complement to the fifth base sequence in forward orientation is transcribed when RNA polymerase only binds to a complement to a second base sequence, wherein the second product comprises a sequence complementary to the fourth base sequence, the first base sequence, the second base sequence, and the third base sequence in reverse transcription when the RNA polymerase only binds to the fifth base sequence, wherein the third product and the fourth product are transcribed when RNA polymerase binds to both promoter sequences of RNA polymerase which are complement to the second base sequence and the fifth base sequence, wherein the third product is transcribed from the complement to the second base sequence comprising the complement to the third base sequence, and wherein the fourth product is transcribed from the fifth base sequence comprising the third base sequence;

step 6 of subjecting the elongation product as a template to digestion with an enzyme;

step 7 of subjecting the reverse transcription product as a template to elongation using the first primer; and step 8 of subjecting the elongation product to transcription with RNA polymerase to detect the sequence that is nonspecific to the target nucleic acid.

3. The method for detecting a target nucleic acid according to claim 1, wherein the first primer further comprises at its 5' end an arbitrary sixth base sequence, and wherein step 4 further comprises:

step 4 of (a) subjecting the elongation product, obtained in step 3, to transcription with RNA polymerase to produce a transcription reaction from the complement to the second base sequence which is the promoter sequence of RNA polymerase and produces a transcript comprising a complement to the third base sequence and a complement to the sixth base sequence; and (b) subjecting a third primer comprising a sequence identical to the sixth base sequence to elongation with an DNA polymerase with strand displacement activity to produce an elongation reaction with an DNA polymerase with strand displacement activity, wherein the DNA polymerase can elongate a strand by unwinding the double-strand DNA and produces an elongation product comprising the complement to the fourth base sequence, the first base sequence, the second base sequence, the third base sequence and the sixth base sequence in reverse orientation;

step 5 of synthesizing a double-strand nucleic acid from the elongation product from the third primer as a template using the second primer; and step 6 of subjecting the double-strand nucleic acid to transcription with RNA polymerase and to nucleic acid synthesis using the third primer and DNA polymerase with strand displacement activity to detect the sequence that is nonspecific to the target nucleic acid.

4. The method for detecting a target nucleic acid according to claim 1, wherein a probe comprising the third base sequence and having at its ends a fluorophore and a quencher bound thereto is allowed to hybridize to the transcription product, and light emitted from the fluorophore is detected.

5. The method for detecting a target nucleic acid according to claim 1, wherein the number of bases constituting the transcription product obtained in step 4 is 20 to 61.

6. The method for detecting a target nucleic acid according to claim 1, wherein no temperature cycle is required.

* * * * *

```
                          SEQUENCE LISTING

<160> NUMBER OF SEQ ID NOS: 16

<210> SEQ ID NO 1
<211> LENGTH: 73
<212> TYPE: DNA
<213> ORGANISM: Artificial Sequence
<220> FEATURE:
<223> OTHER INFORMATION: Inventor: Tanabe, Maiko; Uematsu, Chihiro
<220> FEATURE:
<223> OTHER INFORMATION: Description of Artificial Sequence: designed
      reverse oligonucleotide primer which is used in the amplification
      method and hybridizes with Hepatitis C Virus genotypeU

<400> SEQUENCE: 1
cccttctcac tgttctctca ttctccctat agtgagtcgt attagaattc tcgcaagcac      60
cctatcaggc agt                                                        73

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: designed
      forward oligonucleotide primer which is used in the amplification
      method and hybridizes with Hepatitis C Virus genotypeU

<400> SEQUENCE: 2
gcagaaagcg tctagccatg gcgt                                            24

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: DNA probe
      which is used in detection of amplificated fragments

<400> SEQUENCE: 3
cgacgtccct tctcactgtt ctctcatacg tcg                                  33

<210> SEQ ID NO 4
<211> LENGTH: 93
<212> TYPE: DNA
<213> ORGANISM: Artificial Sequence
<220> FEATURE:
<223> OTHER INFORMATION: Description of Artificial Sequence: designed
      reverse oligonucleotide primer which is used in the amplification
      method and hybridizes with Hepatitis C Virus genotypeU

<400> SEQUENCE: 4
atttaggtga cactatagaa taccactcat ctcttctccc tgtttctccc tatagtgagt     60
```

```
cgtattagaa ttcaagcacc ctatcaggca gta                          93
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: designed
      forward oligonucleotide primer which is used in the amplification
      method and hybridizes with Hepatitis C Virus genotypeU

<400> SEQUENCE: 5

```
gtctagccat ggcgttagta                                         20
```

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: DNA probe
      which is used in detection of amplificated fragments

<400> SEQUENCE: 6

```
cgacgtcact catctcttct ccctgttacg tcg                          33
```

<210> SEQ ID NO 7
<211> LENGTH: 93
<212> TYPE: DNA
<213> ORGANISM: Artificial Sequence
<220> FEATURE:
<223> OTHER INFORMATION: Description of Artificial Sequence: designed
      reverse oligonucleotide primer which is used in the amplification
      method and hybridizes with Hepatitis C Virus genotypeU

<400> SEQUENCE: 7

```
atttaggtga cactatagaa tacctctgtt ccctcatcac ttcttctccc tatagtgagt    60
cgtattagaa ttcaagcacc ctatcaggca gta                          93
```

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: DNA probe
      which is used in detection of amplificated fragments

<400> SEQUENCE: 8

```
cgacgtctct gttccctcat cacttctacg tcg                          33
```

<210> SEQ ID NO 9
<211> LENGTH: 92
<212> TYPE: DNA
<213> ORGANISM: Artificial Sequence
<220> FEATURE:
<223> OTHER INFORMATION: Description of Artificial Sequence: designed
      reverse oligonucleotide primer which is used in the amplification
      method and hybridizes with Human Insulin Gene

<400> SEQUENCE: 9

```
atttaggtga cactatagaa taccccttct ctctcatcac tgtttctccc tatagtgagt    60
cgtattagaa tttagttgca gtagttctcc ag                           92
```

<210> SEQ ID NO 10
<211> LENGTH: 18
<212> TYPE: DNA

```
<213> ORGANISM: Artificial Sequence
<220> FEATURE:
<223> OTHER INFORMATION: Description of Artificial Sequence: designed
      forward oligonucleotide primer which is used in newly method and
      hybridizes with Human Insulin Gene

<400> SEQUENCE: 10
tggtgcaggc agcctgca                                                      18

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: DNA probe
      which is used in detection of amplificated fragments

<400> SEQUENCE: 11
cgacgtccct tctctctcat cactgttacg tcg                                     33

<210> SEQ ID NO 12
<211> LENGTH: 91
<212> TYPE: DNA
<213> ORGANISM: Artificial Sequence
<220> FEATURE:
<223> OTHER INFORMATION: Description of Artificial Sequence: designed
      reverse oligonucleotide primer which is used in newly method and
      hybridizes with Human Papillomavirus DNA

<400> SEQUENCE: 12
atttaggtga cactatagaa taccactcat ccctgttctc ttcttctccc tatagtgagt        60
cgtattagaa ttgtttgcag ctctgtgcat a                                       91

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: designed
      reverse oligonucleotide primer which is used in conventional
      method and hybridizes with Human Papillomavirus DNA

<400> SEQUENCE: 13
aattctaata cgactcacta tagggagagt ttgcagctct gtgcata                      47

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: designed
      forward oligonucleotide primer which is used in newly method and
      hybridizes with Human Papillomavirus DNA

<400> SEQUENCE: 14
aagggcgtaa ccgaaatcgg                                                    20

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: designed
      forward oligonucleotide primer which is used in conventional
      method and hybridizes with Human Papillomavirus DNA

<400> SEQUENCE: 15
```

```
cactcatccc tgttctcttc taagggcgta accgaaatcg g                              41
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: DNA probe
      which is used in detection of amplificated fragments

<400> SEQUENCE: 16

```
cgacgtcact catccctgtt ctcttctacg tcg                                       33
```